United States Patent [19]
Imashiro et al.

[11] Patent Number: 5,637,769
[45] Date of Patent: Jun. 10, 1997

[54] UREA-MODIFIED CARBODIIMIDE AND PROCESS FOR PRODUCTION THEREOF

[75] Inventors: Yasuo Imashiro; Ikuo Takahashi; Naofumi Horie; Takeshi Yamane, all of Tokyo, Japan

[73] Assignee: Nisshinbo Industries, Inc., Tokyo, Japan

[21] Appl. No.: 494,996

[22] Filed: Jun. 27, 1995

[30] Foreign Application Priority Data

Jul. 15, 1994  [JP]  Japan .................... 6-186758

[51] Int. Cl.$^6$ .................... C07C 275/06; C07C 267/00
[52] U.S. Cl. .................... 564/59; 564/47; 564/56; 564/57; 564/58; 564/252
[58] Field of Search .................... 564/252, 59, 58, 564/57, 56, 47

[56] References Cited

U.S. PATENT DOCUMENTS 4,611,083   9/1986   Buethe et al. .................... 560/351
5,079,326   1/1992   Suzuki et al. .................... 528/53

*Primary Examiner*—Shailendra Kumar
*Attorney, Agent, or Firm*—Kubovcik & Kubovcik

[57] ABSTRACT

The present invention provides: a urea-modified carbodiimide represented by the following general formula

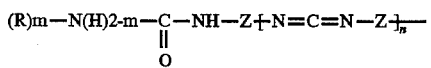

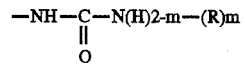

(wherein each R is a $C_1$–$C_{12}$ alkyl group or a $C_3$–$C_{10}$ cycloalkyl group; each Z is a $C_1$–$C_{12}$ alkylene group, a $C_3$–$C_{10}$ cycloalkylene group, a $C_4$–$C_{16}$ alkylene group having a cyclic or non-cyclic structure, or a $C_8$–$C_{16}$ alkylene group having an aromatic ring; n is an integer of 1–50; and each m is an integer of 1 or 2), and a process for producing the above urea-modified carbodiimide, which comprises (1) reacting an organic aliphatic diisocyanate represented by the following general formula $$O=C=N-Z-N=C=O$$

with a primary or secondary organic aliphatic amine to introduce urea bonds into the organic aliphatic diisocyanate and then carbodiimidizing the resulting product in the presence of a carbodiimidization catalyst, or (2) at least partially carbodiimidizing, in the presence of a carbodiimidization catalyst, said organic aliphatic diisocyanate and then reacting the resulting carbodiimide with a primary or secondary organic aliphatic amine to introduce urea bonds into the carbodiimide.

The urea-modified carbodiimide of the present invention is free from the problems of the prior art, has good compatibility with polyester resins and other thermoplastic resins, and can improve the heat resistance and hydrolysis resistance of thermoplastic resins.

9 Claims, No Drawings

UREA-MODIFIED CARBODIIMIDE AND PROCESS FOR PRODUCTION THEREOF

BACKGROUND OF THE INVENTION

1. Field of the Invention

The present invention relates to a urea-modified carbodiimide and a process for production thereof. More particularly, the present invention relates to a urea-modified carbodiimide which has urea bonds in the carbodiimide main chain and thereby has good compatibility with thermoplastic resins and can improve the heat resistance and hydrolysis resistance of thermoplastic resins, as well as to a process for producing said carbodiimide.

2. Description of the Prior Art

Polycarbodiimides have high heat resistance and high reactivity with active hydrogen group, and polycarbodiimides of powdery form, for example, are used as a heat resistance or hydrolysis resistance improver for polyester resins. With respect to examples of application of polycarbodiimides, Japanese Patent Publication No. 15220/1963 discloses a method for improvement of hydrolysis resistance of polyester by addition of aromatic polycarbodiimide compound thereto, and Japanese Patent Application Kokai (Laid-Open) No. 5389/1971 discloses a method for improvement of hydrolysis resistance of polyester by addition of aromatic biscarbodiimide compound thereto.

The above methods for improvement of hydrolysis resistance of polyester utilize a reaction between the carbodiimide group of polycarbodiimide and the active hydrogen of active-hydrogen compound. In the reaction, the terminal carboxyl group of polyester (this carboxyl group is believed to undergo hydrolysis by its self catalysis) is blocked with a carbodiimide compound.

Aromatic polycarbodiimides, when added to a polyester resin of high polymerization degree and high melting point (e.g. a polyethylene terephthalate of industrial use), cause, owing to the high reactivity, a side reaction such as dimerization of carbodiimide group. It invites a reduction in properties, associated with gelling and, moreover, fails to achieve sufficient blocking of terminal carboxyl group, and the resulting improvement in hydrolysis resistance is very small. Therefore, said side reaction must be suppressed, for example, by introducing a group having a steric hindrance effect, to prevent the dimerization of carbodiimide group, as disclosed in the above-mentioned Japanese Patent Publication No. 15220/1963.

Aromatic polycarbodiimides have also a problem in that, when added at high temperatures, they evaporate the component isocyanate and/or aromatic amine, adversely affecting the workers and the working environment.

It is thought that the above-mentioned problems of aromatic polycarbodiimides can be alleviated by the use of aliphatic polycarbodiimides. However, aliphatic polycarbodiimides show no sufficient addition effect to thermoplastic resins for the reasons of, for example, low reactivity as compared with aromatic polycarbodiimides; moreover, aliphatic polycarbodiimides generally have inferior compatibility with resins such as polyester.

SUMMARY OF THE INVENTION

The objects of the present invention are to provide a urea-modified carbodiimide which is free from the problems of the prior art, has good compatibility with polyester and other thermoplastic resins, and can improve the heat resistance and hydrolysis resistance of thermoplastic resins; and a process for production of said carbodiimide.

The present inventors made a study by paying attention to a fact that the bonds or functional groups such as ester bond, amide bond, urethane bond, amino group, hydroxyl group and the like, contained in thermoplastic resins (e.g. polyester, polyamide, polyurethane and copolymers thereof) have polarity or bondability with hydrogen. As a result, the present inventors found out that a urea-modified carbodiimide obtained by introducing urea bonds having a bondability with hydrogen and being capable of interacting with above functional groups, into the carbodiimide main chain, has improved compatibility with said thermoplastic resins. The finding has led to the completion of the present invention.

According to the present invention, there is provided a urea-modified carbodiimide represented by the following general formula

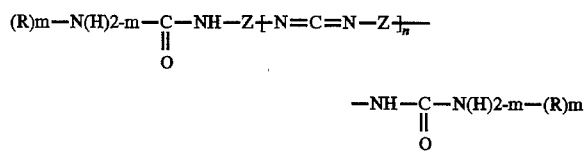

(wherein each R is a $C_1$–$C_{12}$ alkyl group or a $C_3$–$C_{10}$ cycloalkyl group; each Z is a $C_1$–$C_{12}$ alkylene group, a $C_3$–$C_{10}$ cycloalkylene group, a $C_4$–$C_{16}$ alkylene group having a cyclic or non-cyclic structure, or a $C_8$–$C_{16}$ alkylene group having an aromatic ring; n is an integer of 1–50; and each m is an integer of 1 or 2).

According to the present invention, there is also provided a process for producing the above urea-modified carbodiimide, which comprises (1) reacting an organic aliphatic diisocyanate represented by the following general formula

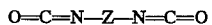

(wherein Z has the same definition as given above) with a primary or secondary organic aliphatic amine to introduce urea bonds into the organic aliphatic diisocyanate and then carbodiimidizing the resulting product in the presence of a carbodiimidization catalyst, or (2) at least partially carbodiimidizing, in the presence of a carbodiimidization catalyst, said organic aliphatic diisocyanate and then reacting the resulting carbodiimide with a primary or secondary organic aliphatic amine to introduce urea bonds into the carbodiimide.

DETAILED DESCRIPTION OF THE INVENTION

The present invention is hereinafter described in detail.

The urea-modified carbodiimide of the present invention is obtained by introducing urea bonds to the terminals of carbodiimide chain, as is clear from the above-mentioned general formula. The raw material monomer constituting said carbodiimide chain is an organic diisocyanate, particularly an organic aliphatic diisocyanate represented by the following general formula

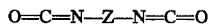

(wherein Z is a $C_1$–$C_{12}$ alkylene group, a $C_3$–$C_{10}$ cycloalkylene group, a $C_4$–$C_{16}$ alkylene group having a cyclic or non-cyclic structure, or a $C_8$–$C_{16}$ alkylene group having an aromatic ring). Therefore, each Z in the main chain of carbodiimide is a group obtained by removing isocyanate groups from the organic aliphatic diisocyanate. Incidentally, in the above organic aliphatic diisocyanate, isocyanate groups are directly bonded to an aliphatic hydrocarbon; and the aliphatic hydrocarbon moiety may contain an aromatic ring as long as the aromatic ring makes no direct bonding to the isocyanate groups.

In the present invention, the organic aliphatic diisocyanate can be exemplified by butane-1,4-diisocyanate, hexamethylene diisocyanate, 2,2,4-trimethylhexamehtylene diisocyanate, cyclohexane-1,4-diisocyanate, xylylene diisocyanate, isophorone diisocyanate, 4,4'-dicyclohexylmethane diisocyanate, 1,3-bis(isocyanatomethyl) cyclohexane, methylcyclohexane diisocyanate, tetramethylxylylene diisocyanate. Of these, preferred are isophorone diisocyanate, 4,4'-dicyclohexylmethane diisocyanate and tetramethylxylylene diisocyanate.

In the urea-modified carbodiimide of the present invention, Zs may be the same or different.

In the present invention, when isophorone diisocyanate is used as the organic aliphatic diisocyanate, each Z in the urea-modified carbodiimide is as follows.

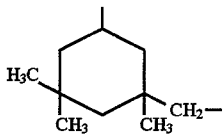

In the urea-modified carbodiimide of the present invention, each R is derived from the primary or secondary amine used in the production of said carbodiimide, and is a $C_1$–$C_{12}$ alkyl group or a $C_3$–$C_{10}$ cycloalkyl group. Specific examples of the primary or secondary amine are organic aliphatic amines such as 2-ethylhexylamine, 2-ethylhexyloxypropylamine, 3-diethythylaminopropylamine, 3-methoxypropylamine, 3-ethylaminopropylamine, dibutylaminopropylamine, n-butyl-amine, t-butylamine, sec-butylamine, cyclohexylamine, diethylamine, diisopropylamine, di-2-ethylhexylamine, diisobutylamine, di- n-butylamine, dicyclohexylamine and the like. Of these, preferred are n-butylamine, di-n-butylamine, cyclohexylamine and dicyclohexylamine, all of which are easily available industrially.

Needless to explain, when the primary or secondary amine is, for example, n-butylamine or di-n-butylamine, each R in the present urea-modified carbodiimide is an n-butyl group.

Rs in the present urea-modified carbodiimide may be the same or different.

Each m in the terminal amino group moieties is an integer of 1 or 2. When each m is 1, the urea bonds in the present urea-modified carbodiimide are derived from a primary amine; and when each m is 2, the urea bonds are derived from a secondary amine.

n in the carbodiimide chain of the present urea-modified carbodiimide indicates the polymerization degree of the carbodiimide chain, and is an integer of 1–50. When n is too large, the resulting urea-modified carbodiimide comes to have too large a viscosity and may fail to have practical applicability.

Next, description is made in detail on the process for production of the present urea-modified carbodiimide having the above-mentioned basic structure.

The present urea-modified carbodiimide having the above-mentioned features can be produced by, as shown by the following reaction scheme, reacting the above-mentioned organic aliphatic diisocyanate with a primary or secondary amine to introduce urea bonds into said diisocyanate and then carbodiimidizing the reaction product in the presence of a carbodiimidization catalyst.

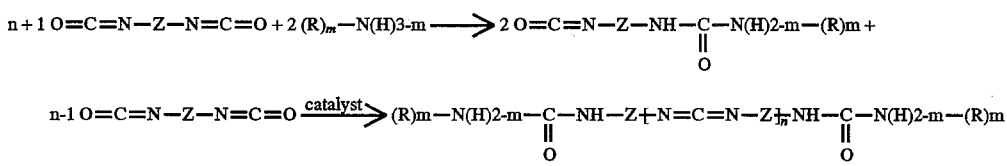

The present urea-modified carbodiimide can also be produced by, as shown by the following reaction scheme, at least partially carbodiimidizing the above-mentioned organic aliphatic diisocyanate in the presence of a carbodiimidization catalyst and then reacting the resulting carbodiimide with a primary or secondary amine to introduce urea bonds into the carbodiimide.

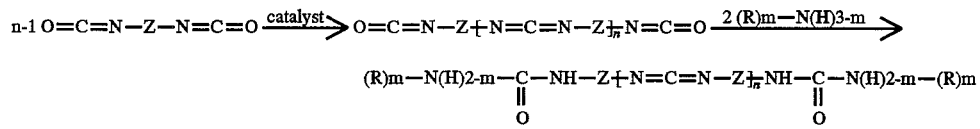

In the above production, the molar ratio of the organic aliphatic diisocyanate and the primary or secondary organic aliphatic amine is, for example, 1:1 to 51:2, and the number of carbodiimide groups is 1–50.

The carbodiimidization of the organic aliphatic diisocyanate or the urea bond-introduced organic aliphatic diisocyanate can be conducted basically by the conventional process for production of polycarbodiimide [see e.g. U.S. Pat. No. 2,941,956; Japanese Patent Publication No. 33279/1972; J. Org. Chem., Vol. 28, pp. 2069–2075 (1963); Chemical review, 1981, Vol. 81, No. 4, pp. 619–621].

The carbodiimidization of the organic aliphatic diisocyanate or the urea bond-introduced organic aliphatic diisocyanate proceeds in the presence of a carbodiimidization catalyst. As said catalyst, there can be used 1-phenyl-2-phospholene-1-oxide, 1-methyl-2-phospholene-1-oxide, 1-ethyl-2-phospholene-1-oxide, 3-methyl-1-phenyl-2-phospholene-1-oxide and 3-phospholene isomers thereof. 3-Methyl-1-phenyl-2-phospholene-1-oxide is preferred in view of the reactivity.

The temperature of the carbodiimidization is preferably about 80°–180° C. When the temperature is lower than the above range, a very long reaction time is required. When the temperature is higher than the above range, side reactions take place, making it impossible to obtain a urea-modified carbodiimide imide of high quality.

In order to complete the reaction quickly, the carbodiimidization is conducted in a stream of an inert gas such as nitrogen or the like.

The addition reaction between the organic aliphatic diisocyanate and the primary or secondary organic aliphatic amine can be allowed to proceed easily only by heating. The reaction temperature can be about 30°–140° C., preferably about 50°–120° C. When the reaction temperature is lower than the above range, a very long reaction time is required. When the reaction temperature is higher than the above range, side reactions take place, making it impossible to obtain a urea-modified carbodiimide of high quality.

The thus-obtained urea-modified carbodiimide can be used in various forms. When added to a thermoplastic resin or the like, it is preferably ground using a grinder and then used.

Addition of the present urea-modified carbodiimide to a thermoplastic resin can be conducted by known methods. In the most preferable method, a urea-modified carbodiimide of ground form is added to and mixed with a thermoplastic resin of molten state, in given proportions. It is also preferable to mix a thermoplastic resin of chip form and a urea-modified carbodiimide of ground form in given proportions by the use of a conventional mixer and then melt-mixing the mixture.

The present invention is hereinafter described in more detail by way of Examples.

Production of urea-modified carbodiimides

EXAMPLE 1

146 g of n-butylamine was dropwise added to 2,442 g of isophorone diisocyanate at 50° C. in 1 hour to introduce urea bonds into the diisocyanate. Thereto was added 24.4 g of a carbodiimidization catalyst (3-methyl-1-phenyl-2-phospholene-1-oxide), and carbodiimidization was conducted at 180° C. for 70 hours to obtain a yellow transparent urea-modified carbodiimide (number of carbodiimide groups=10). The urea-modified carbodiimide was cooled and ground using a roll granulator.

EXAMPLE 2

258 g of di-n-butylamine was dropwise added to 2,442 g of isophorone diisocyanate at 50° C. in 1 hour to introduce urea bonds into the diisocyanate. Thereto was added 24.4 g of a carbodiimidization catalyst (3-methyl-1-phenyl-2-phospholene-1-oxide), and carbodiimidization was conducted at 180° C. for 72 hours to obtain a yellow transparent urea-modified carbodiimide (number of carbodiimide groups=10). The urea-modified carbodiimide was cooled and ground using a roll granulator.

EXAMPLE 3

362 g of dicyclohexylamine was dropwise added to 2,442 g of isophorone diisocyanate at 50° C. in 1 hour to introduce urea bonds into the diisocyanate. Thereto was added 24.4 g of a carbodiimidization catalyst (3-methyl-1-phenyl-2-phospholene-1-oxide), and carbodiimidization was conducted at 180° C. for 68 hours to obtain a yellow transparent urea-modified carbodiimide (number of carbodiimide groups=10). The urea-modified carbodiimide was cooled and ground using a roll granulator.

EXAMPLE 4

645 g of di-n-butylamine was dropwise added to 1,110 g of isophorone diisocyanate at 50° C. in 1 hour to introduce urea bonds into the diisocyanate. Thereto was added 11.1 g of a carbodiimidization catalyst (3-methyl-1-phenyl-2-phospholene-1-oxide), and carbodiimidization was conducted at 180° C. for 36 hours to obtain a yellow transparent urea-modified carbodiimide (number of carbodiimide groups=1). The urea-modified carbodiimide was cooled and ground using a roll granulator.

EXAMPLE 5

258 g of di-n-butylamine was dropwise added to 880 g of isophorone diisocyanate at 50° C. in 1 hour to introduce urea bonds into the diisocyanate. Thereto was added 8.9 g of a carbodiimidization catalyst (3-methyl-1-phenyl-2-phospholene-1-oxide), and carbodiimidization was conducted at 180° C. for 54 hours to obtain a yellow transparent urea-modified carbodiimide (number of carbodiimide groups=3). The urea-modified carbodiimide was cooled and ground using a roll granulator.

EXAMPLE 6

129 g of di-n-butylamine was dropwise added to 2,331 g of isophorone diisocyanate at 50° C. in 1 hour to introduce urea bonds into the diisocyanate. Thereto was added 23.3 g of a carbodiimidization catalyst (3-methyl-1-phenyl-2-phospholene-1-oxide), and carbodiimidization was conducted at 180° C. for 96 hours to obtain a yellow transparent urea-modified carbodiimide (number of carbodiimide groups=20). The urea-modified carbodiimide was cooled and ground using a roll granulator.

EXAMPLE 7

146 g of n-butylamine was dropwise added to 2,882 g of 4,4'-dicyclohexylmethane diisocyanate at 50° C. in 2 hours to introduce urea bonds into the diisocyanate. Thereto was added 28.8 g of a carbodiimidization catalyst (3-methyl-1-phenyl-2-phospholene-1-oxide), and carbodiimidization was conducted at 180° C. for 93 hours to obtain a yellow transparent urea-modified carbodiimide (number of carbodiimide groups=10). The urea-modified carbodiimide was cooled and ground using a roll granulator.

EXAMPLE 8

258 g of di-n-butylamine was dropwise added to 2,882 g of 4,4'-dicyclohexylmethane diisocyanate at 50° C. in 2 hours to introduce urea bonds into the diisocyanate. Thereto was added 28.8 g of a carbodiimidization catalyst (3-methyl-1-phenyl-2-phospholene-1-oxide), and carbodiimidization was conducted at 180° C. for 96 hours to obtain a yellow transparent urea-modified carbodiimide (number of carbodiimide groups =10). The urea-modified carbodiimide was cooled and ground using a roll granulator.

EXAMPLE 9

362 g of dicyclohexylamine was dropwise added to 2,882 g of 4,4'-dicyclohexylmethane diisocyanate at 50° C. in 1.5 hours to introduce urea bonds into the diisocyanate. Thereto was added 28.8 g of a carbodiimidization catalyst (3-methyl-1-phenyl-2-phospholene-1-oxide), and carbodiimidization was conducted ducted at 180° C. for 90 hours to obtain a yellow transparent urea-modified carbodiimide (number of carbodiimide groups=10). The urea-modified carbodiimide was cooled and ground using a roll granulator.

EXAMPLE 10

645 g of di-n-butylamine was dropwise added to 1,310 g of 4,4'-dicyclohexylmethane diisocyanate at 50° C. in 2 hours to introduce urea bonds into the diisocyanate. Thereto was added 13.1 g of a carbodiimidization catalyst (3-methyl-1-phenyl-2-phospholene-1-oxide), and carbodiimidization was conducted at 180° C. for 48 hours to obtain a yellow transparent urea-modified carbodiimide (number of carbodiimide groups=1). The urea-modified carbodiimide was cooled and ground using a roll granulator.

EXAMPLE 11

258 g of di-n-butylamine was dropwise added to 1,048 g of 4,4'-dicyclohexylmethane diisocyanate at 50° C. in 2 hours to introduce urea bonds into the diisocyanate. Thereto was added 10.5 g of a carbodiimidization catalyst (3-methyl-1-phenyl-2-phospholene-1-oxide), and carbodiimidization was conducted at 180° C. for 62 hours to obtain a yellow transparent urea-modified carbodiimide (number of carbodiimide groups=3). The urea-modified carbodiimide was cooled and ground using a roll granulator.

EXAMPLE 12

129 g of di-n-butylamine was dropwise added to 2,331 g of 4,4'-dicyclohexylmethane diisocyanate at 50° C. in 2 hours to introduce urea bonds into the diisocyanate. Thereto was added 27.5 g of a carbodiimidization catalyst (3-methyl-1-phenyl-2-phospholene-1-oxide), and carbodiimidization was conducted at 180° C. for 120 hours to obtain a yellow transparent urea-modified carbodiimide (number of carbodiimide groups=20). The urea-modified modified carbodiimide was cooled and ground using a roll granulator.

EXAMPLE 13

258 g of di-n-butylamine was dropwise added to 2,684 g of m-tetramethylxylylene diisocyanate at 50° C. in 4 hours to introduce urea bonds into the diisocyanate. Thereto was added 26.8 g of a carbodiimidization catalyst (3-methyl-1-phenyl-2-phospholene-1-oxide), and carbodiimidization was conducted at 180° C. for 120 hours to obtain a brown transparent urea-modified carbodiimide (number of carbodiimide groups=10).

EXAMPLE 14

645 g of di-n-butylamine was dropwise added to 1,220 g of m-tetramethylxylylene diisocyanate at 50° C. in 4 hours to introduce urea bonds into the diisocyanate. Thereto was added 12.2 g of a carbodiimidization catalyst (3-methyl-1-phenyl-2-phospholene-1-oxide), and carbodiimidization was conducted at 180° C. for 72 hours to obtain a brown transparent urea-modified carbodiimide (number of carbodiimide groups=1).

EXAMPLE 15

258 g of di-n-butylamine was dropwise added to 976 g of m-tetramethylxylylene diisocyanate at 50° C. in 4 hours to introduce urea bonds into the diisocyanate. Thereto was added 9.8 g of a carbodiimidization catalyst (3-methyl-1-phenyl-2-phospholene-1-oxide), and carbodiimidization was conducted at 180° C. for 96 hours to obtain a brown transparent urea-modified carbodiimide (number of carbodiimide groups=3).

EXAMPLE 16

129 g of di-n-butylamine was dropwise added to 2,562 g of m-tetramethylxylylene diisocyanate at 50° C. in 4 hours to introduce urea bonds into the diisocyanate. Thereto was added 25.6 g of a carbodiimidization catalyst (3-methyl-1-phenyl-2-phospholene-1-oxide), and carbodiimidization was conducted at 180° C. for 144 hours to obtain a brown transparent urea-modified carbodiimide (number of carbodiimide groups=20).

EXAMPLE 17

2,442 g of isophorone diisocyanate was reacted with 24.4 g of a carbodiimidization catalyst (3-methyl-1-phenyl-2-phospholene-1-oxide) at 180° C. for 16 hours to obtain a carbodiimide containing 4.20% of NCO groups. The carbodiimide was cooled to 80° C. Thereto was dropwise added 258 g of di-n-butylamine to give rise to a reaction for 1 hour to obtain a yellow transparent urea-modified carbodiimide (number of carbodiimide groups=10). The urea-modified carbodiimide was cooled and ground using a roll granulator.

EXAMPLE 18

2,882 g of 4,4'-dicyclohexylmethane diisocyanate was reacted with 28.8 g of a carbodiimidization catalyst (3-methyl-1-phenyl-2-phospholene-1-oxide) at 180° C. for 24 hours to obtain a carbodiimide containing 3.44% of NCO groups. The carbodiimide was cooled to 80° C. Thereto was dropwise added 258 g of di-n-butylamine to give rise to a reaction for 2 hours to obtain a yellow transparent urea-modified carbodiimide (number of carbodiimide groups=10). The urea-modified carbodiimide was cooled and ground using a roll granulator.

EXAMPLE 19

2,684 g of m-tetramethylxylylene diisocyanate was reacted with 26.8 g of a carbodiimidization catalyst (3-methyl-1-phenyl-2- phospholene-1-oxide) at 180° C. for 32 hours to obtain a carbodiimide containing 3.74% of NCO groups. The carbodiimide was cooled to 80° C. Thereto was dropwise added 258 g of di-n-butylamine to give rise to a reaction for 2 hours to obtain a brown transparent urea-modified carbodiimide (number of carbodiimide groups=10).

Effect of addition of urea-modified carbodiimides to thermoplastic resins

Reference Example 1

A polyethylene terephthalate (EFG-7, a product of Kanebo, Ltd.) and one of the urea-modified carbodiimides obtained in Examples 1–19 were melt-mixed at 270° C. by the use of a twin-screw extruder to prepare a compound containing 1% of said urea-modified carbodiimide. The compound was subjected to injection molding to prepare ASTM No. 1 dumbbells (thickness=3 mm). The dumbbells were crystallized at 120° C. for 2 hours, then subjected to a dry heat treatment at 120° C. for given lengths of time (0, 10, 30 and 60 days), and measured for tensile strength and elongation. Dumbbells containing no urea-modified carbodiimide were also prepared and subjected to the same measurements.

Comparative Reference Example 1

The procedure of Reference Example 1 was repeated except that the urea-modified carbodiimide used in Reference Example 1 was replaced by 1,3,5-triisopropylbenzene polycarbodiimide (molecular weight=about 2,000).

Comparative Reference Example 2

The procedure of Reference Example 1 was repeated except that the urea-modified carbodiimide used in Reference Example 1 was replaced by isophorone polycarbodiimide (molecular weight=about 2,000).

The test results of Reference Example 1 (Examples 1–19) and Comparative Reference Examples 1 and 2 are shown in Table 1.

TABLE 1

| Days | Tensile strength (kg/cm$^2$) | | | | Elongation (%) | | | |
|---|---|---|---|---|---|---|---|---|
| | 0 | 10 | 30 | 60 | 0 | 10 | 30 | 60 |
| Example 1 | 623 | 664 | 663 | 681 | 4.2 | 4.5 | 4.5 | 4.6 |
| Example 2 | 622 | 665 | 660 | 685 | 4.3 | 4.5 | 4.6 | 4.5 |
| Example 3 | 621 | 666 | 662 | 665 | 4.3 | 4.6 | 4.5 | 4.8 |
| Example 4 | 619 | 658 | 655 | 659 | 4.1 | 4.3 | 4.3 | 4.2 |
| Example 5 | 620 | 659 | 660 | 658 | 4.2 | 4.5 | 4.6 | 4.3 |
| Example 6 | 625 | 655 | 660 | 658 | 4.3 | 4.6 | 4.8 | 4.9 |
| Example 7 | 621 | 666 | 658 | 685 | 4.3 | 4.4 | 4.8 | 4.9 |
| Example 8 | 620 | 668 | 659 | 691 | 4.4 | 4.6 | 5.0 | 5.0 |
| Example 9 | 622 | 665 | 660 | 680 | 4.3 | 4.5 | 4.9 | 4.8 |
| Example 10 | 618 | 660 | 661 | 658 | 4.1 | 4.6 | 4.4 | 4.3 |
| Example 11 | 620 | 660 | 658 | 662 | 4.3 | 4.5 | 4.8 | 4.8 |
| Example 12 | 625 | 665 | 661 | 685 | 4.4 | 4.5 | 4.9 | 5.0 |
| Example 13 | 621 | 659 | 658 | 655 | 4.2 | 4.5 | 4.5 | 4.2 |
| Example 14 | 620 | 658 | 655 | 648 | 4.2 | 4.4 | 4.2 | 4.1 |
| Example 15 | 620 | 659 | 656 | 649 | 4.3 | 4.5 | 4.2 | 4.2 |
| Example 16 | 621 | 660 | 659 | 658 | 4.3 | 4.6 | 4.3 | 4.2 |
| Example 17 | 622 | 665 | 661 | 683 | 4.3 | 4.4 | 4.5 | 4.4 |
| Example 18 | 623 | 663 | 661 | 685 | 4.4 | 4.5 | 4.9 | 5.0 |
| Example 19 | 620 | 657 | 655 | 653 | 4.2 | 4.5 | 4.3 | 4.2 |
| Comparative Example 1 | 610 | 625 | 605 | 590 | 4.1 | 4.3 | 3.9 | 3.2 |
| Comparative Example 2 | 620 | 653 | 634 | 627 | 4.2 | 4.4 | 4.1 | 3.8 |
| No addition | 630 | 665 | 618 | 523 | 4.2 | 4.6 | 3.4 | 2.6 |

Reference Example 2

The dumbbells prepared in Reference Example 1 and Comparative Reference Examples 1 and 2 were subjected to a dry heat treatment at 150° C. for given lengths of time (0, 14, 21 and 28 days) and measured for tensile strength and elongation. The results are shown in Table 2.

TABLE 2

| Days | Tensile strength (kg/cm$^2$) | | | | Elongation (%) | | | |
|---|---|---|---|---|---|---|---|---|
| | 0 | 14 | 21 | 28 | 0 | 14 | 21 | 28 |
| Example 1 | 623 | 668 | 662 | 680 | 4.2 | 4.5 | 4.5 | 4.4 |
| Example 2 | 622 | 668 | 660 | 683 | 4.3 | 4.6 | 4.4 | 4.3 |
| Example 3 | 621 | 669 | 661 | 675 | 4.3 | 4.6 | 4.6 | 4.4 |
| Example 4 | 619 | 651 | 653 | 650 | 4.1 | 4.2 | 4.1 | 3.9 |
| Example 5 | 620 | 660 | 662 | 657 | 4.2 | 4.3 | 4.2 | 4.0 |
| Example 6 | 625 | 659 | 663 | 665 | 4.3 | 4.4 | 4.4 | 4.1 |
| Example 7 | 621 | 987 | 679 | 693 | 4.3 | 4.8 | 4.8 | 4.7 |
| Example 8 | 620 | 695 | 676 | 698 | 4.4 | 5.2 | 4.9 | 4.6 |
| Example 9 | 622 | 667 | 672 | 691 | 4.3 | 4.9 | 4.8 | 4.5 |
| Example 10 | 618 | 661 | 661 | 648 | 4.1 | 4.3 | 4.4 | 4.3 |
| Example 11 | 620 | 665 | 664 | 668 | 4.3 | 5.0 | 4.6 | 4.2 |
| Example 12 | 625 | 664 | 669 | 681 | 4.4 | 5.4 | 4.9 | 4.7 |
| Example 13 | 621 | 651 | 641 | 640 | 4.2 | 4.5 | 4.0 | 3.7 |
| Example 14 | 620 | 652 | 642 | 648 | 4.2 | 4.3 | 4.1 | 3.6 |
| Example 15 | 620 | 651 | 639 | 631 | 4.3 | 4.4 | 4.2 | 3.9 |
| Example 16 | 621 | 649 | 651 | 658 | 4.3 | 4.6 | 4.2 | 4.0 |
| Example 17 | 622 | 658 | 665 | 688 | 4.3 | 4.7 | 4.6 | 4.4 |
| Example 18 | 623 | 667 | 670 | 686 | 4.4 | 5.3 | 4.9 | 4.9 |
| Example 19 | 620 | 655 | 644 | 641 | 4.2 | 4.3 | 4.0 | 3.8 |
| Comparative Example 1 | 610 | 598 | 552 | 514 | 4.1 | 3.7 | 3.0 | 2.5 |
| Comparative Example 2 | 620 | 641 | 509 | 592 | 4.2 | 4.3 | 3.9 | 3.3 |
| No addition | 630 | 381 | 282 | 254 | 4.2 | 1.6 | 1.3 | 1.3 |

Reference Example 3

The dumbbells prepared in Reference Example 1 and Comparative Reference Examples 1 and 2 were subjected to a wet heat treatment at 80° C. and 90% R.H. for given lengths of time (0, 10, 30 and 60 days) and measured for tensile strength and elongation. The results are shown in Table 3.

TABLE 3

| Days | Tensile strength (kg/cm$^2$) | | | | Elongation (%) | | | |
|---|---|---|---|---|---|---|---|---|
| | 0 | 10 | 30 | 60 | 0 | 10 | 30 | 60 |
| Example 1 | 623 | 640 | 640 | 646 | 4.2 | 4.0 | 4.1 | 3.7 |
| Example 2 | 622 | 642 | 638 | 649 | 4.3 | 4.1 | 4.1 | 3.8 |
| Example 3 | 621 | 641 | 639 | 648 | 4.3 | 4.2 | 4.0 | 3.8 |
| Example 4 | 619 | 635 | 631 | 633 | 4.1 | 4.0 | 3.6 | 3.7 |
| Example 5 | 620 | 640 | 639 | 635 | 4.2 | 4.1 | 4.0 | 3.9 |
| Example 6 | 625 | 647 | 640 | 646 | 4.3 | 4.2 | 4.2 | 4.1 |
| Example 7 | 621 | 649 | 635 | 649 | 4.3 | 4.1 | 4.2 | 4.3 |
| Example 8 | 620 | 648 | 632 | 650 | 4.4 | 4.2 | 4.1 | 4.4 |
| Example 9 | 622 | 650 | 640 | 651 | 4.3 | 4.3 | 4.2 | 4.3 |
| Example 10 | 618 | 645 | 631 | 639 | 4.1 | 4.3 | 4.0 | 4.1 |
| Example 11 | 620 | 646 | 633 | 642 | 4.3 | 4.0 | 4.1 | 4.2 |
| Example 12 | 625 | 650 | 645 | 651 | 4.4 | 4.4 | 4.2 | 4.5 |
| Example 13 | 621 | 642 | 630 | 630 | 4.2 | 4.1 | 4.0 | 3.8 |
| Example 14 | 620 | 635 | 628 | 625 | 4.2 | 4.0 | 3.8 | 3.5 |
| Example 15 | 620 | 636 | 630 | 628 | 4.3 | 3.9 | 4.0 | 3.7 |
| Example 16 | 621 | 639 | 633 | 630 | 4.3 | 4.0 | 3.8 | 3.9 |
| Example 17 | 622 | 641 | 633 | 642 | 4.3 | 4.0 | 4.1 | 4.1 |
| Example 18 | 623 | 647 | 635 | 649 | 4.4 | 4.3 | 4.1 | 4.4 |
| Example 19 | 620 | 641 | 628 | 628 | 4.2 | 4.0 | 4.0 | 3.8 |
| Comparative Example 1 | 610 | 624 | 603 | 587 | 4.1 | 3.8 | 3.5 | 2.9 |
| Comparative Example 2 | 620 | 629 | 622 | 608 | 4.2 | 4.0 | 3.5 | 3.2 |
| No addition | 630 | 646 | 591 | 455 | 4.2 | 4.0 | 3.1 | 2.1 |

Reference Example 4

A polyurethane (F-30T, a product of Nisshinbo Industries, Inc.) and the urea-modified carbodiimide obtained in Example 2, 8 or 13 were melt-mixed at 200° C. by the use of a twin-screw extruder to prepare a compound containing 1% of said urea-modified carbodiimide. The compound was subjected to injection molding to prepare ASTM No. 1 dumbbells (thickness=3 mm). The dumbbells were subjected to a dry heat treatment at 120° C. for given lengths of time and then measured for tensile strength. Dumbbells containing no urea-modified carbodiimide were also prepared and subjected to the same measurement.

Comparative Reference Example 3

The procedure of Reference Example 4 was repeated except that the urea-modified carbodiimide used in Reference Example 4 was replaced by 1,3,5-triisopropylbenzene polycarbodiimide (molecular weight=about 2,000).

Comparative Reference Example 4

The procedure of Reference Example 4 was repeated except that the urea-modified carbodiimide used in Reference Example 4 was replaced by isophorone polycarbodiimide (molecular weight=about 2,000).

The test results of Reference Example 4 and Comparative Reference Examples 3 and 4 are shown in Table 4.

TABLE 4

| Days | Tensile strength (kg/cm²) | | | |
|---|---|---|---|---|
| | 0 | 10 | 30 | 60 |
| Example 2 | 219 | 230 | 195 | 186 |
| Example 8 | 212 | 233 | 199 | 192 |
| Example 13 | 208 | 227 | 194 | 188 |
| Comparative Example 3 | 248 | 160 | 92 | 59 |
| Comparative Example 4 | 223 | 207 | 169 | 143 |
| No addition | 227 | 181 | 155 | 68 |

Reference Example 5

The dumbbells prepared in Reference Example 4 and Comparative Reference Examples 3 and 4 were subjected to a wet heat treatment at 80° C. and 90% R.H. for given lengths of time (0, 10, 30 and 60 days) and measured for tensile strength. The results are shown in Table 5.

TABLE 5

| Days | Tensile strength (kg/cm²) | | | |
|---|---|---|---|---|
| | 0 | 10 | 30 | 60 |
| Example 2 | 219 | 220 | 199 | 136 |
| Example 8 | 212 | 221 | 207 | 141 |
| Example 13 | 208 | 217 | 194 | 137 |
| Comparative Example 3 | 248 | 210 | 106 | 5 |
| Comparative Example 4 | 223 | 215 | 159 | 96 |
| No addition | 227 | 196 | 116 | — |

Reference Example 6

A nylon 66 (A100N, a product of Unitika Ltd.) and the urea-modified carbodiimide obtained in Example 2, 8 or 13 were melt-mixed at 280° C. by the use of a twin-screw extruder to prepare a compound containing 2% of said urea-modified carbodiimide. The compound was subjected to injection molding to prepare ASTM No. 1 dumbbells (thickness=3mm). The dumbbells were subjected to a hot water (70° C.) treatment for given lengths of time (0, 7, 14 and 28 days) and then measured for tensile strength. Dumbbells containing no urea-modified carbodiimide were also prepared and subjected to the same measurement.

Comparative Reference Example 5

The procedure of Reference Example 6 was repeated except that the urea-modified carbodiimide used in Reference Example 6 was replaced by 1,3,5-triisopropylbenzene polycarbodiimide (molecular weight=about 2,000).

Comparative Reference Example 6

The procedure of Reference Example 6 was repeated except that the urea-modified carbodiimide used in Reference Example 6 was replaced by isophorone polycarbodiimide (molecular weight=about 2,000).

The test results of Reference Example 6 and Comparative Reference Examples 5 and 6 are shown in Table 6.

TABLE 6

| Days | Tensile strength (kg/cm²) | | | |
|---|---|---|---|---|
| | 0 | 10 | 30 | 60 |
| Example 2 | 471 | 364 | 338 | 331 |
| Example 8 | 475 | 371 | 342 | 339 |
| Example 13 | 481 | 369 | 341 | 340 |
| Comparative Example 3 | 473 | 321 | 305 | 296 |
| Comparative Example 4 | 476 | 340 | 321 | 315 |
| No addition | 489 | 219 | 227 | 215 |

As is clear from Tables 1–6, the urea-modified carbodiimide of the present invention has good compatibility with thermoplastic resins and therefore, when added to said resins, can improve the heat resistance and hydrolysis resistance of said resins without causing deterioration of properties of said resins.

What is claimed is:

1. A urea-modified carbodiimide represented by the following general formula

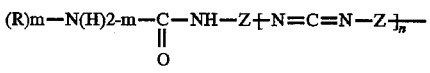

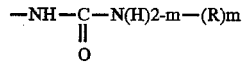

(wherein each R is a $C_1$–$C_{12}$ alkyl group or a $C_3$–$C_{10}$ cycloalkyl group; each Z is a $C_1$–$C_{12}$ alkylene group, a $C_3$–$C_{10}$ cycloalkylene group, a $C_4$–$C_{16}$ alkylene group having a cyclic or non-cyclic structure, or a $C_8$–$C_{16}$ alkylene group having an aromatic ring; n is an integer of 1–50; and each m is an integer of 1 or 2).

2. A urea-modified carbodiimide according to claim 1, wherein each Z is a residue obtained by removing isocyanate groups from isophorone diisocyanate, 4,4'-dicyclohexylmethane diisocyanate or tetramethylxylylene diisocyanate.

3. A urea-modified carbodiimide according to claim 1, wherein Zs may be the same or different.

4. A urea-modified carbodiimide according to claim 1, wherein each R is a n-butyl group or a cyclohexyl group.

5. A urea-modified carbodiimide according to claim 1, wherein Rs may be the same or different.

6. A urea-modified carbodiimide according to claim 2, wherein Zs may be the same or different.

7. A urea-modified carbodiimide according to claim 2, wherein Rs may be the same or different.

8. A urea-modified carbodiimide according to claim 3, wherein Rs may be the same or different.

9. A urea-modified carbodiimide according to claim 4, wherein Rs may be the same or different.

* * * * *